(12) United States Patent  (10) Patent No.: US 7,652,177 B2
Sakamoto et al.  (45) Date of Patent: Jan. 26, 2010

(54) PROCESS FOR PRODUCTION OF ALCOHOL COMPOUND

(75) Inventors: Toru Sakamoto, Toyonaka (JP); Shinzo Seko, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/307,240

(22) PCT Filed: Jul. 3, 2007

(86) PCT No.: PCT/JP2007/063288

§ 371 (c)(1),
(2), (4) Date: Dec. 31, 2008

(87) PCT Pub. No.: WO2008/004543

PCT Pub. Date: Jan. 10, 2008

(65) Prior Publication Data

US 2009/0192336 A1 Jul. 30, 2009

(30) Foreign Application Priority Data

Jul. 4, 2006 (JP) ............... 2006-184253

(51) Int. Cl.
*C07C 33/18* (2006.01)
*C07C 33/46* (2006.01)
*C07C 33/28* (2006.01)
(52) U.S. Cl. ............... 568/715; 568/812; 568/813
(58) Field of Classification Search ............ 568/715, 568/812, 813
See application file for complete search history.

(56) References Cited

U.S. PATENT DOCUMENTS 5,872,137 A 2/1999 Sakamoto et al.

FOREIGN PATENT DOCUMENTS

| CN | 1860874 A | 11/2006 |
| JP | 8-337549 A | 12/1996 |
| WO | WO-2004/048320 A1 | 6/2004 |

*Primary Examiner*—Sikarl A Witherspoon
(74) *Attorney, Agent, or Firm*—Birch, Stewart, Kolasch & Birch, LLP

(57) ABSTRACT

A process for the production of an alcohol compound represented by the formula (3):

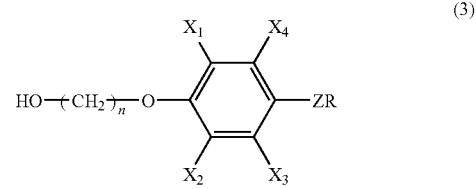

wherein $X_1$, $X_2$, $X_3$, $X_4$, Z, R and n are as defined below, comprising reacting a phenol represented by the formula (1):

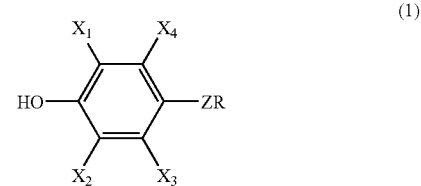

wherein $X_1$, $X_2$, $X_3$ and $X_4$ independently represent a hydrogen atom, a halogen atom or an alkyl group having 1 to 3 carbon atoms; Z represents an oxygen atom or a sulfur atom; and R represents a halogen-substituted alkenyl group, with a haloalcohol represented by the formula (2):

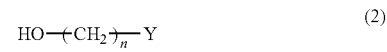

wherein Y represents a chlorine atom or a bromine atom; and n represents an integer of 2 or 3, in a biphase system composed of a water-immiscible organic solvent and an aqueous alkali metal hydroxide solution in the presence of a phase-transfer catalyst.

18 Claims, No Drawings

PROCESS FOR PRODUCTION OF ALCOHOL COMPOUND

TECHNICAL FIELD

The present invention relates to a process for production of an alcohol compound useful as an intermediate for producing an active ingredient of insecticides.

BACKGROUND ART

For production of a 3-(2,6-dichloro-4-(3,3-dichloro-2-propenyloxy)phenoxy)-1-propyl alcohol, which is an intermediate for producing dihalopropene compounds having insecticidal activity, there is a known process which comprises reacting 1,3-dibromopropane and 2,6-dichloro-4-(3,3-dichloro-2-propenyloxy)phenol in N,N-dimethylformamide in the presence of potassium carbonate to produce 3,5-dichloro-4-(3-bromopropyloxy)-1-(3,3-dichloro-2-propenyloxy)benzene, reacting the product with benzoic acid in N,N-dimethylformamide in the presence of potassium carbonate to produce 3,5-dichloro-4-(3-benzoyloxypropyloxy)-1-(3,3-dichloro-2-propenyloxy)benzene, and hydrolyzing the product to produce 3-(2,6-dichloro-4-(3,3-dichloro-2-propenyloxy)phenoxy)-1-propyl alcohol, as shown in the following scheme (Scheme 1, Patent Document 1).

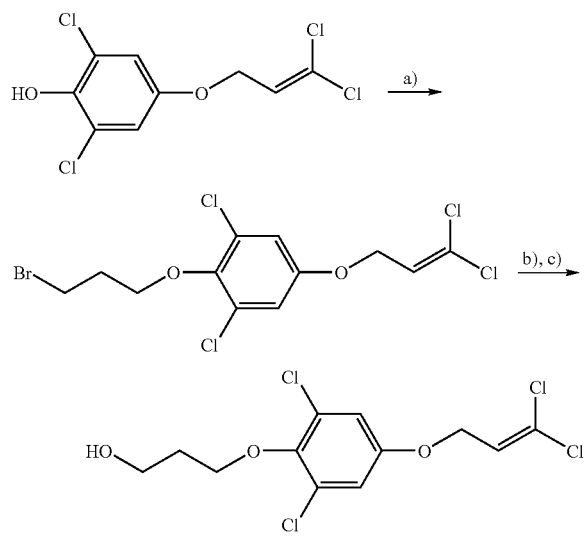

Scheme 1 a) 1,3-dibromobutane, potassium carbonate, N,N-dimethylformamide, b) benzoic acid, potassium carbonate, N,N-dimethylformamide, c) aqueous potassium hydroxide solution, methanol.

Patent Document 1: JP-A 08-337549

DISCLOSURE OF THE INVENTION

Problem to be Solved by the Invention

The above process requires multiple steps to produce the intended alcohol compound, and therefore it is complicated.

The present invention provides a process for efficient production of the intended alcohol compound comprising fewer steps.

Means for Solving the Problem

The present invention provides a process for production of an alcohol compound represented by the formula (3):

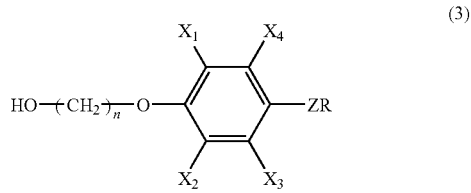

wherein $X_1$, $X_2$, $X_3$ and $X_4$ independently represent a hydrogen atom, a halogen atom or an alkyl group having 1 to 3 carbon atoms, Z represents an oxygen atom or a sulfur atom, R represents a halogen-substituted alkenyl group, and n represents an integer of 2 or 3, which comprises reacting a phenol represented by the formula (1):

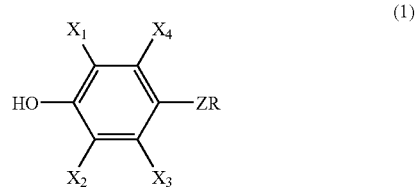

wherein $X_1$, $X_2$, $X_3$, $X_4$, Z and R are as defined above, with a haloalcohol represented by the formula (2):

wherein Y represents a chlorine atom or a bromine atom, and n is as defined above, in a biphase system composed of a water-immiscible organic solvent and an aqueous alkali metal hydroxide solution in the presence of a phase-transfer catalyst.

EFFECTS OF THE INVENTION

According to the process of the present invention, the alcohol compound represented by the formula (3) which is useful as an intermediate for producing an active ingredient of an insecticide can be produced efficiently with fewer steps.

BEST MODE FOR CARRYING OUT THE INVENTION

The present invention will be described below.

Substituents represented by $X_1$, $X_2$, $X_3$ and $X_4$ in the formulae (1) and (3) are described. Examples of the halogen atom represented by $X_1$, $X_2$, $X_3$ or $X_4$ include a fluorine atom, a chlorine atom, a bromine atom and an iodine atom. Examples of the alkyl group having 1 to 3 carbon atoms represented by $X_1$, $X_2$, $X_3$ or $X_4$ include a methyl group, an ethyl group, an n-propyl group and an iso-propyl group. Z is preferably an oxygen atom.

In the formulae (1) and (3), examples of the halogen-substituted alkenyl group represented by R include alkenyl groups substituted with halogen atom(s) such as a fluorine atom, a chlorine atom, a bromine atom or an iodine atom. A typical example thereof is a 3,3-dihalopropenyl group.

Specific examples of the halogen-substituted alkenyl group include a 3,3-difluoro-2-propenyl group, a 3,3-dichloro-2-propenyl group, a 3-bromo-3-chloro-2-propenyl group and a 3,3-dibromopropenyl group. R is preferably a 3,3-dichloro-2-propenyl group.

Examples of the phenol represented by the formula (1) include, but not limited to, 4-(3,3-difluoro-2-propenyloxy)phenol, 4-(3,3-dichloro-2-propenyloxy)phenol, 4-(3-bromo-3-chloro-2-propenyloxy)phenol, 4-(3,3-dibromo-2-propenyloxy)phenol, 2-fluoro-4-(3,3-dichloro-2-propenyloxy)phenol, 3-fluoro-4-(3,3-dichloro-2-propenyloxy)phenol, 2,5-difluoro-4-(3,3-dichloro-2-propenyloxy)phenol, 2-chloro-4-(3,3-dichloro-2-propenyloxy)phenol, 3-chloro-4-(3,3-dichloro-2-propenyloxy)phenol, 2,5-dichloro-4-(3,3-dichloro-2-propenyloxy)phenol, 2,3,5-trichloro-4-(3,3-dichloro-2-propenyloxy)phenol, 2,3,5,6-tetrachloro-4-(3,3-dichloro-2-propenyloxy)phenol, 2,5-dibromo-4-(3,3-dichloro-2-propenyloxy)phenol, 2,5-diiodo-4-(3,3-dichloro-2-propenyloxy)phenol, 2-methyl-4-(3,3-dichloro-2-propenyloxy)phenol, 2-ethyl-4-(3,3-dichloro-2-propenyloxy)phenol, 2-n-propyl-4-(3,3-dichloro-2-propenyloxy)phenol, 2-iso-propyl-4-(3,3-dichloro-2-propenyloxy)phenol, and 2,5-dichloro-4-(3,3-dichloro-2-propenylthio)phenol.

In the formula (2), Y preferably represents a bromine atom and n preferably represents an integer of 3. Examples of the haloalcohol represented by the formula (2) include 2-chloro-1-ethanol, 3-chloro-1-propanol, 2-bromo-1-ethanol and 3-bromo-1-propanol. Preferred is 3-bromo-1-propanol.

Examples of the water-immiscible organic solvent used in the reaction include hydrocarbon compounds. Specific examples thereof include aliphatic hydrocarbon compounds such as hexane, heptane or the like, aromatic hydrocarbon compounds such as toluene, xylene, monochlorobenzene or the like, and their mixtures. Other examples of the water-immiscible organic solvent include chain ether compounds such as diethyl ether, methyl-tert-butyl ether or the like, and their mixtures. As the water-immiscible organic solvent, preferably hydrocarbon compounds or chain ether compounds are used. From the viewpoint of versatility, toluene is more preferably used.

The amount of the water-immiscible organic solvent used is not specifically limited. From the viewpoint of volume efficiency, the amount of the water-immiscible organic solvent used is usually 0.1 parts by weight to 20 parts by weight per 1 part by weight of the phenol represented by the formula (1).

Examples of the aqueous alkali metal hydroxide solution used in the reaction include aqueous solutions of lithium hydroxide, sodium hydroxide and potassium hydroxide. The amount of the alkaline metal hydroxide used is usually 0.9 mol to 3 mol per 1 mol of the phenol represented by the formula (1). The concentration of alkali metal hydroxide in the aqueous alkali metal hydroxide solution is not specifically limited, and is usually 2% by weight to 10% by weight.

Examples of the phase-transfer catalyst include quaternary ammonium salts such as tetra-n-butylammonium chloride, tetra-n-butylammonium bromide, tetra-n-butylammonium iodide, tetra-n-butylammonium sulfate, triethylbenzylammonium chloride, trioctylmethylammonium chloride or the like, quaternary phosphonium salts such as trimethylphenylphosphonium bromide or the like, and pyridinium salts such as n-dodecylpyridinium chloride or the like. When the reaction is performed in the presence of such a phase-transfer catalyst, the alcohol compound represented by the formula (3) is produced in good yield. From the viewpoints of availability and versatility, a tetra-n-butylammonium salt such as tetra-n-butylammonium chloride, tetra-n-butylammonium bromide, tetra-n-butylammonium iodide or tetra-n-butylammonium sulfate is preferably used as the phase-transfer catalyst.

The amount of the phase-transfer catalyst used is not specifically limited. Considering economic efficiency and the like, the phase-transfer catalyst is usually used in an amount of 0.01 mol to 0.2 mol per 1 mol of the phenol represented by the formula (1).

The order of mixing the phenol represented by the formula (1), the haloalcohol represented by the formula (2), the water-immiscible organic solvent, the aqueous alkali metal hydroxide solution and the phase-transfer catalyst is not specifically limited. For example, these materials may be mixed all at once and stirred to react. Alternatively, to an aqueous mixture solution of the phenol and the aqueous alkali metal hydroxide solution may be added dropwise a mixture solution of the haloalcohol and the water-immiscible organic solvent. An aqueous mixture solution of the phenol and the aqueous alkali metal hydroxide solution can be also added dropwise to a mixture solution of the haloalcohol and the water-immiscible organic solvent.

The reaction can be performed at a temperature from a room temperature to a refluxing temperature. The reaction temperature is usually from a room temperature to 100° C. From the viewpoint of a reaction rate, the reaction is preferably performed within the range of 50° C. to 100° C. The reaction time is usually about 10 hours to about 20 hours. Progress of the reaction can be monitored by analyzing the residual amount of the phenol represented by the formula (1) using gas chromatography or liquid chromatography.

After the end of the reaction, a reaction mixture is usually allowed to stand and separated to give an oil layer containing the intended product, the alcohol compound represented by the formula (3). The oil layer can be washed with water. The oil layer also can be neutralized with acidic water such as aqueous sulfuric acid or the like, separated, and washed with water again.

After washing, for example, the obtained oil layer can be concentrated under reduced pressure to remove the organic solvent to give a concentrate of the alcohol compound represented by the formula (3). The concentrate can be further subjected to general purification such as silica gel column chromatography, crystallization and recrystallization, if necessary.

As described above, the intended alcohol compound represented by the formula (3) can be produced efficiently in good yield. Examples of the compound represented by the formula (3) include the following compounds.

$$HO-(CH_2)_n-O-C_6(X_1)(X_2)(X_3)(X_4)-ZR \quad (3)$$

| No. | n | X$_1$ | X$_2$ | X$_3$ | X$_4$ | Z | R |
|---|---|---|---|---|---|---|---|
| 1 | 2 | H | H | H | H | O | CH$_2$CH=CCl$_2$ |
| 2 | 2 | H | H | H | H | O | CH$_2$CH=CBr$_2$ |
| 3 | 2 | H | H | H | H | S | CH$_2$CH=CH$_2$ |
| 4 | 2 | H | H | H | H | S | CH$_2$CH=CCl$_2$ |
| 5 | 2 | H | H | H | H | S | CH$_2$CH=CBr$_2$ |
| 6 | 2 | F | F | H | H | O | CH$_2$CH=CCl$_2$ |
| 7 | 2 | F | F | H | H | O | CH$_2$CH=CBr$_2$ |
| 8 | 2 | F | F | H | H | S | CH$_2$CH=CCl$_2$ |
| 9 | 2 | F | F | H | H | S | CH$_2$CH=CBr$_2$ |
| 10 | 2 | F | Cl | H | H | O | CH$_2$CH=CCl$_2$ |
| 11 | 2 | F | Cl | H | H | O | CH$_2$CH=CBr$_2$ |
| 12 | 2 | F | Cl | H | H | S | CH$_2$CH=CCl$_2$ |
| 13 | 2 | F | Cl | H | H | S | CH$_2$CH=CBr$_2$ |
| 14 | 2 | F | Br | H | H | O | CH$_2$CH=CCl$_2$ |
| 15 | 2 | F | Br | H | H | O | CH$_2$CH=CBr$_2$ |
| 16 | 2 | F | Br | H | H | S | CH$_2$CH=CCl$_2$ |
| 17 | 2 | F | Br | H | H | S | CH$_2$CH=CBr$_2$ |
| 18 | 2 | F | CH$_3$ | H | H | O | CH$_2$CH=CCl$_2$ |
| 19 | 2 | F | CH$_3$ | H | H | O | CH$_2$CH=CBr$_2$ |
| 20 | 2 | F | CH$_3$ | H | H | S | CH$_2$CH=CCl$_2$ |
| 21 | 2 | F | CH$_3$ | H | H | S | CH$_2$CH=CBr$_2$ |
| 22 | 2 | Cl | Cl | H | H | O | CH$_2$CH=CCl$_2$ |
| 23 | 2 | Cl | Cl | H | H | O | CH$_2$CH=CBr$_2$ |
| 24 | 2 | Cl | Cl | H | H | S | CH$_2$CH=CCl$_2$ |
| 25 | 2 | Cl | Cl | H | H | S | CH$_2$CH=CBr$_2$ |
| 26 | 2 | Cl | Br | H | H | O | CH$_2$CH=CCl$_2$ |
| 27 | 2 | Cl | Br | H | H | O | CH$_2$CH=CBr$_2$ |
| 28 | 2 | Cl | Br | H | H | S | CH$_2$CH=CCl$_2$ |
| 29 | 2 | Cl | Br | H | H | S | CH$_2$CH=CBr$_2$ |
| 30 | 2 | Cl | CH$_3$ | H | H | O | CH$_2$CH=CCl$_2$ |
| 31 | 2 | Cl | CH$_3$ | H | H | O | CH$_2$CH=CBr$_2$ |
| 32 | 2 | Cl | CH$_3$ | H | H | S | CH$_2$CH=CCl$_2$ |
| 33 | 2 | Cl | CH$_3$ | H | H | S | CH$_2$CH=CBr$_2$ |
| 34 | 2 | Br | Br | H | H | O | CH$_2$CH=CCl$_2$ |
| 35 | 2 | Br | Br | H | H | O | CH$_2$CH=CBr$_2$ |
| 36 | 2 | Br | Br | H | H | S | CH$_2$CH=CCl$_2$ |
| 37 | 2 | Br | Br | H | H | S | CH$_2$CH=CBr$_2$ |
| 38 | 2 | Br | CH$_3$ | H | H | O | CH$_2$CH=CCl$_2$ |
| 39 | 2 | Br | CH$_3$ | H | H | O | CH$_2$CH=CBr$_2$ |
| 40 | 2 | Br | CH$_3$ | H | H | S | CH$_2$CH=CCl$_2$ |
| 41 | 2 | Br | CH$_3$ | H | H | S | CH$_2$CH=CBr$_2$ |
| 42 | 2 | CH$_3$ | CH$_3$ | H | H | O | CH$_2$CH=CCl$_2$ |
| 43 | 2 | CH$_3$ | CH$_3$ | H | H | O | CH$_2$CH=CBr$_2$ |
| 44 | 2 | CH$_3$ | CH$_3$ | H | H | S | CH$_2$CH=CCl$_2$ |
| 45 | 2 | CH$_3$ | CH$_3$ | H | H | S | CH$_2$CH=CBr$_2$ |
| 46 | 2 | F | F | F | H | O | CH$_2$CH=CCl$_2$ |
| 47 | 2 | F | F | F | H | O | CH$_2$CH=CBr$_2$ |
| 48 | 2 | F | F | F | H | S | CH$_2$CH=CCl$_2$ |
| 49 | 2 | F | F | F | H | S | CH$_2$CH=CBr$_2$ |
| 50 | 2 | F | F | F | F | O | CH$_2$CH=CCl$_2$ |
| 51 | 2 | F | F | F | F | O | CH$_2$CH=CBr$_2$ |
| 52 | 2 | F | F | F | F | S | CH$_2$CH=CCl$_2$ |
| 53 | 2 | F | F | F | F | S | CH$_2$CH=CBr$_2$ |
| 54 | 2 | Cl | Cl | Cl | H | O | CH$_2$CH=CCl$_2$ |
| 55 | 2 | Cl | Cl | Cl | H | O | CH$_2$CH=CBr$_2$ |
| 56 | 2 | Cl | Cl | Cl | H | S | CH$_2$CH=CCl$_2$ |
| 57 | 2 | Cl | Cl | Cl | H | S | CH$_2$CH=CBr$_2$ |
| 58 | 2 | Cl | Cl | Cl | Cl | O | CH$_2$CH=CCl$_2$ |
| 59 | 2 | Cl | Cl | Cl | Cl | O | CH$_2$CH=CBr$_2$ |
| 60 | 2 | Cl | Cl | Cl | Cl | S | CH$_2$CH=CCl$_2$ |
| 61 | 2 | Cl | Cl | Cl | Cl | S | CH$_2$CH=CBr$_2$ |
| 62 | 3 | H | H | H | H | O | CH$_2$CH=CCl$_2$ |
| 63 | 3 | H | H | H | H | O | CH$_2$CH=CBr$_2$ |
| 64 | 3 | H | H | H | H | S | CH$_2$CH=CH$_2$ |
| 65 | 3 | H | H | H | H | S | CH$_2$CH=CCl$_2$ |
| 66 | 3 | H | H | H | H | S | CH$_2$CH=CBr$_2$ |
| 67 | 3 | F | F | H | H | O | CH$_2$CH=CCl$_2$ |
| 68 | 3 | F | F | H | H | O | CH$_2$CH=CBr$_2$ |
| 69 | 3 | F | F | H | H | S | CH$_2$CH=CCl$_2$ |
| 70 | 3 | F | F | H | H | S | CH$_2$CH=CBr$_2$ |
| 71 | 3 | F | Cl | H | H | O | CH$_2$CH=CCl$_2$ |
| 72 | 3 | F | Cl | H | H | O | CH$_2$CH=CBr$_2$ |
| 73 | 3 | F | Cl | H | H | S | CH$_2$CH=CCl$_2$ |
| 74 | 3 | F | Cl | H | H | S | CH$_2$CH=CBr$_2$ |
| 75 | 3 | F | Br | H | H | O | CH$_2$CH=CCl$_2$ |
| 76 | 3 | F | Br | H | H | O | CH$_2$CH=CBr$_2$ |
| 77 | 3 | F | Br | H | H | S | CH$_2$CH=CCl$_2$ |
| 78 | 3 | F | Br | H | H | S | CH$_2$CH=CBr$_2$ |
| 79 | 3 | F | CH$_3$ | H | H | O | CH$_2$CH=CCl$_2$ |
| 80 | 3 | F | CH$_3$ | H | H | O | CH$_2$CH=CBr$_2$ |
| 81 | 3 | F | CH$_3$ | H | H | S | CH$_2$CH=CCl$_2$ |
| 82 | 3 | F | CH$_3$ | H | H | S | CH$_2$CH=CBr$_2$ |
| 83 | 3 | Cl | Cl | H | H | O | CH$_2$CH=CCl$_2$ |
| 84 | 3 | Cl | Cl | H | H | O | CH$_2$CH=CBr$_2$ |
| 85 | 3 | Cl | Cl | H | H | S | CH$_2$CH=CCl$_2$ |
| 86 | 3 | Cl | Cl | H | H | S | CH$_2$CH=CBr$_2$ |
| 87 | 3 | Cl | Br | H | H | O | CH$_2$CH=CCl$_2$ |
| 88 | 3 | Cl | Br | H | H | O | CH$_2$CH=CBr$_2$ |
| 89 | 3 | Cl | Br | H | H | S | CH$_2$CH=CCl$_2$ |
| 90 | 3 | Cl | Br | H | H | S | CH$_2$CH=CBr$_2$ |
| 91 | 3 | Cl | CH$_3$ | H | H | O | CH$_2$CH=CCl$_2$ |
| 92 | 3 | Cl | CH$_3$ | H | H | O | CH$_2$CH=CBr$_2$ |
| 93 | 3 | Cl | CH$_3$ | H | H | S | CH$_2$CH=CCl$_2$ |
| 94 | 3 | Cl | CH$_3$ | H | H | S | CH$_2$CH=CBr$_2$ |
| 95 | 3 | Br | Br | H | H | O | CH$_2$CH=CCl$_2$ |
| 96 | 3 | Br | Br | H | H | O | CH$_2$CH=CBr$_2$ |
| 97 | 3 | Br | Br | H | H | S | CH$_2$CH=CCl$_2$ |
| 98 | 3 | Br | Br | H | H | S | CH$_2$CH=CBr$_2$ |
| 99 | 3 | Br | CH$_3$ | H | H | O | CH$_2$CH=CCl$_2$ |
| 100 | 3 | Br | CH$_3$ | H | H | O | CH$_2$CH=CBr$_2$ |
| 101 | 3 | Br | CH$_3$ | H | H | S | CH$_2$CH=CCl$_2$ |
| 102 | 3 | Br | CH$_3$ | H | H | S | CH$_2$CH=CBr$_2$ |
| 103 | 3 | CH$_3$ | CH$_3$ | H | H | O | CH$_2$CH=CCl$_2$ |
| 104 | 3 | CH$_3$ | CH$_3$ | H | H | O | CH$_2$CH=CBr$_2$ |
| 105 | 3 | CH$_3$ | CH$_3$ | H | H | S | CH$_2$CH=CCl$_2$ |
| 106 | 3 | CH$_3$ | CH$_3$ | H | H | S | CH$_2$CH=CBr$_2$ |
| 107 | 3 | F | F | F | H | O | CH$_2$CH=CCl$_2$ |
| 108 | 3 | F | F | F | H | O | CH$_2$CH=CBr$_2$ |
| 109 | 3 | F | F | F | H | S | CH$_2$CH=CCl$_2$ |
| 110 | 3 | F | F | F | H | S | CH$_2$CH=CBr$_2$ |
| 111 | 3 | F | F | F | F | O | CH$_2$CH=CCl$_2$ |
| 112 | 3 | F | F | F | F | O | CH$_2$CH=CBr$_2$ |
| 113 | 3 | F | F | F | F | S | CH$_2$CH=CCl$_2$ |
| 114 | 3 | F | F | F | F | S | CH$_2$CH=CBr$_2$ |
| 115 | 3 | Cl | Cl | Cl | H | O | CH$_2$CH=CCl$_2$ |
| 116 | 3 | Cl | Cl | Cl | H | O | CH$_2$CH=CBr$_2$ |
| 117 | 3 | Cl | Cl | Cl | H | S | CH$_2$CH=CCl$_2$ |
| 118 | 3 | Cl | Cl | Cl | H | S | CH$_2$CH=CBr$_2$ |
| 119 | 3 | Cl | Cl | Cl | Cl | O | CH$_2$CH=CCl$_2$ |
| 120 | 3 | Cl | Cl | Cl | Cl | O | CH$_2$CH=CBr$_2$ |
| 121 | 3 | Cl | Cl | Cl | Cl | S | CH$_2$CH=CCl$_2$ |
| 122 | 3 | Cl | Cl | Cl | Cl | S | CH$_2$CH=CBr$_2$ |

EXAMPLE 1

Hereinafter, the present invention will be further described in more detail with reference to Examples, which the present invention is not limited to.

EXAMPLE 1

To a mixture of 0.72 g of 3-bromopropanol, 1.0 g of 2,6-dichloro-4-(3,3-dichloro-2-propenyloxy)phenol, 5.0 g of toluene, 0.06 g of tetra-n-butylammonium bromide and 5.0 g of water was added 0.77 q of a 27% aqueous sodium hydroxide solution, The mixture was heated to 60° C. and stirred for 8 hours. The reaction mixture was then cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.2 g of 3-(2,6-dichloro-4-(3,3-dichloro-2-propenyloxy)phenoxy)-1-propyl alcohol (purity: 92%, yield: 93%).

EXAMPLE 2

To a mixture of 0.72 g of 3-bromopropanol, 1.0 g of 2,6-dichloro-4-(3,3-dichloro-2-propenyloxy)phenol, 5.0 g of toluene, 0.04 g of tetra-n-butylammonium chloride and 5.0 g of water was added 0.77 g of a 27% aqueous sodium hydroxide solution. The mixture was heated to 60° C. and stirred for 14 hours. The reaction mixture was then cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.1 g of 3-(2,6-dichloro-4-(3,3-dichloro-2-propenyloxy)phenoxy)-1-propyl alcohol (purity: 93%, yield: 82%).

EXAMPLE 3

To a mixture of 0.72 g of 3-bromopropanol, 1.0 g of 2,6-dichloro-4-(3,3-dichloro-2-propenyloxy)phenol, 5.0 g of toluene, 0.10 g of trioctylmethylammonium chloride and 5.0 g of water was added 0.77 g of a 27% aqueous sodium hydroxide solution. The mixture was heated to 60° C. and stirred for 20 hours. The reaction mixture was then cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.1 g of 3-(2,6-dichloro-4-(3,3-dichloro-2-propenyloxy)phenoxy)-1-propyl alcohol (purity: 85%, yield: 76%).

EXAMPLE 4

To a mixture of 0.72 g of 3-bromopropanol, 1.0 g of 2,6-dichloro-4-(3,3-dichloro-2-propenyloxy)phenol, 5.0 g of hexane, 0.06 g of tetra-n-butylammonium bromide and 5.0 g of water was added 0.77 g of a 27% aqueous sodium hydroxide solution. The mixture was heated to 60° C. and stirred for 4 hours. The reaction mixture was then cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.2 g of 3-(2,6-dichloro-4-(3,3-dichloro-2-propenyloxy)phenoxy)-1-propyl alcohol (purity: 92%, yield: 89%).

EXAMPLE 5

To a mixture of 0.72 g of 3-bromopropanol, 1.0 g of 2,6-dichloro-4-(3,3-dichloro-2-propenyloxy)phenol, 3.0 g of hexane, 2.0 g of toluene, 0.06 g of tetra-n-butylammonium bromide and 5.0 g of water was added 0.77 g of a 27% aqueous sodium hydroxide solution. The mixture was heated to 60° C. and stirred for 4 hours. The reaction mixture was then cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.2 g of 3-(2,6-dichloro-4-(3,3-dichloro-2-propenyloxy)phenoxy)-1-propyl alcohol (purity: 93%, yield: 90%).

EXAMPLE 6

To a mixture of 0.72 g of 3-bromopropanol, 1.0 g of 2,6-dichloro-4-(3,3-dichloro-2-propenyloxy)phenol, 5.0 g of t-butyl methyl ether, 0.06 g of tetra-n-butylammonium bromide and 5.0 g of water was added 0.77 g of a 27% aqueous sodium hydroxide solution. The mixture was heated to 60° C. and stirred for 12 hours. The reaction mixture was then cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.2 g of 3-(2,6-dichloro-4-(3,3-dichloro-2-propenyloxy)phenoxy)-1-propyl alcohol (purity: 93%, yield: 90%).

EXAMPLE 7

A mixture of 0.53 g of 3-bromopropanol, 5.0 g of toluene and 0.06 g of tetra-n-butylammonium bromide was heated to 60° C. Thereto was added dropwise a mixed solution of 1.0 g of 2,6-dichloro-4-(3,3-dichloro-2-propenyloxy)phenol, 5.0 g of water and 0.51 g of a 27% aqueous sodium hydroxide solution with stirring over 6 hours. After completion of the addition, the mixture was further stirred at 60° C. for 4 hours. The reaction mixture was then cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.1 g of 3-(2,6-dichloro-4-(3,3-dichloro-2-propenyloxy)phenoxy)-1-propyl alcohol (purity: 94%, yield: 86%).

EXAMPLE 8

A mixture of 0.53 g of 3-bromopropanol, 5.0 g of toluene and 0.06 q of tetra-n-butylammonium bromide was heated to 60° C. Thereto was added dropwise a mixed solution of 1.0 q of 2,6-dichloro-4-(3,3-dichloro-2-propenyloxy)phenol, 5.0 g of water and 0.16 g of lithium hydroxide monohydrate with stirring over 6 hours. After completion of the addition, the mixture was further stirred at 60° C. for 10 hours. The reaction mixture was then cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.1 g of 3-(2,6-dichloro-4-(3,3-dichloro-2-propenyloxy)phenoxy)-1-propyl alcohol (purity: 93%, yield: 84%).

EXAMPLE 9

A reaction and a workup were performed with a similar procedure to that described in Example 8 except that 1.1 g of a 20% aqueous potassium hydroxide solution was used instead of 0.16 g of lithium hydroxide monohydrate, to give 1.1 g of 3-(2,6-dichloro-4-(3,3-dichloro-2-propenyloxy)phenoxy)-1-propyl alcohol (purity: 93%, yield: 84%).

EXAMPLE 10

A mixture of 0.53 g of 3-bromopropanol, 5.0 g of toluene and 0.06 g of tetra-n-butylammonium iodide was heated to 60° C. Thereto was added dropwise a mixed solution of 1.0 g of 2,6-dichloro-4-(3,3-dichloro-2-propenyloxy)phenol, 5.0 g of water and 0.51 g of a 27% aqueous sodium hydroxide solution with stirring over 6 hours. After completion of the addition, the mixture was further stirred at 60° C. for 10 hours. The reaction mixture was then cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.1 g of 3-(2,6-dichloro-4-(3,3-dichloro-2-propenyloxy)phenoxy)-1-propyl alcohol (purity: 94%, yield: 86%).

EXAMPLE 11

A mixture of 0.53 g of 3-bromopropanol, 5.0 g of toluene and 0.06 g of tetra-n-butylammonium sulfate was heated to 60° C. Thereto was added dropwise a mixed solution of 1.0 g of 2,6-dichloro-4-(3,3-dichloro-2-propenyloxy)phenol, 5.0 g of water and 0.54 g of a 27% aqueous sodium hydroxide solution with stirring over 6 hours. After completion of the addition, the mixture was further stirred at 60° C. for 4 hours. Then 0.10 g of 3-bromopropanol and 0.10 g of a 27% aqueous sodium hydroxide solution were added thereto, and the mixture was further stirred for 10 hours. The reaction mixture was then cooled to 20° C. After 2.0 g of a 20% aqueous sulfuric acid solution and 4.3 g of toluene were added thereto, the mixture was stirred and then separated. The obtained organic layer was washed with 5.0 g of water and concentrated under reduced pressure to give 1.2 q of 3-(2,6-dichloro-4-(3,3-dichloro-2-propenyloxy)phenoxy)-1-propyl alcohol (purity: 89%, yield: 91%).

EXAMPLE 12

A mixture of 0.53 g of 3-bromopropanol, 5.0 g of toluene and 0.06 g of trimethylphenylphosphonium bromide was heated to 60° C. Thereto was added dropwise a mixed solution of 1.0 g of 2,6-dichloro-4-(3,3-dichloro-2-propenyloxy) phenol, 5.0 g of water and 0.54 g of a 27% aqueous sodium hydroxide solution with stirring over 6 hours. After completion of the addition, the mixture was further stirred at 60° C. for 4 hours. Then 0.10 g of 3-bromopropanol and 0.10 g of a 27% aqueous sodium hydroxide solution were added thereto, and the mixture was further stirred for 7 hours. The reaction mixture was then cooled to 20° C. After 2.0 g of a 20% aqueous sulfuric acid solution and 5.0 g of toluene were added thereto, the mixture was stirred and then separated. The obtained organic layer was washed with 5.0 g of water and concentrated under reduced pressure to give 1.2 g of 3-(2,6-dichloro-4-(3,3-dichloro-2-propenyloxy)phenoxy)-1-propyl alcohol (purity: 90%, yield: 91%).

EXAMPLE 13

A mixture of 0.53 g of 3-bromopropanol, 5.0 g of toluene and 0.05 g of n-dodecylpyridinium chloride was heated to 60° C. Thereto was added dropwise a mixed solution of 1.0 g of 2,6-dichloro-4-(3,3-dichloro-2-propenyloxy)phenol, 5.0 g of water and 0.54 g of a 27% aqueous sodium hydroxide solution with stirring over 6 hours. After completion of the addition, the mixture was further stirred at 60° C. for 11 hours. In this period, 0.10 g of 3-bromopropanol and 0.10 g of a 27% aqueous sodium hydroxide solution were further added thereto at each time point of 4 and 7 hours. Then, the reaction mixture was cooled to 20° C. After 2.0 g of a 20% aqueous sulfuric acid solution and 5.0 g of toluene were added thereto, the mixture was stirred and then separated. The obtained organic layer was washed with 5.0 g of water and concentrated under reduced pressure to give 1.3 g of 3-(2,6-dichloro-4-(3,3-dichloro-2-propenyloxy)phenoxy)-1-propyl alcohol (purity: 85%, yield: 89%).

EXAMPLE 14

A mixture of 0.37 g of 3-chloropropanol, 5.0 g of toluene and 0.06 g of tetra-n-butylammonium iodide was heated to 80° C. Thereto was added dropwise a mixed solution of 1.0 g of 2,6-dichloro-4-(3,3-dichloro-2-propenyloxy)phenol, 5.0 g of water and 0.51 g of a 27% aqueous sodium hydroxide solution with stirring over 6 hours. After completion of the addition, the mixture was further stirred at 80° C. for 20 hours. In this period, 0.20 g of 3-chloropropanol was further added at each time point of 7, 9, 12 and 17 hours, and 0.20 g of a 27% aqueous sodium hydroxide solution was further added at each time point of 12 and 17 hours. Then, the reaction mixture was cooled to 20° C. After 2.0 g of a 20% aqueous sulfuric acid solution was added thereto, the mixture was stirred and then separated. The obtained organic layer was washed with 5.0 g of water and concentrated under reduced pressure to give 1.0 g of 3-(2,6-dichloro-4-(3,3-dichloro-2-propenyloxy)phenoxy)-1-propyl alcohol (purity: 87%, yield: 73%).

EXAMPLE 15

A mixture of 0.48 g of 2-bromoethanol, 5.0 g of toluene and 0.06 g of tetra-n-butylammonium bromide was heated to 60° C. Thereto was added dropwise a mixed solution of 1.0 g of 2,6-dichloro-4-(3,3-dichloro-2-propenyloxy)phenol, 5.0 g of water and 0.54 g of a 27% aqueous sodium hydroxide solution with stirring over 6 hours. After completion of the addition, the mixture was further stirred at 60° C. for 25 hours. In this period, 0.10 g of 2-bromoethanol and 0.10 g of a 27% aqueous sodium hydroxide solution were further added at the time point of 7 hours, 0.40 g of 2-bromoethanol and 0.30 g of a 27% aqueous sodium hydroxide solution were further added at the time point of 13 hours, and 0.40 g of 2-bromoethanol and 0.30 g of a 27% aqueous sodium hydroxide solution were further added at the time point of 20 hours. Then, the reaction mixture was cooled to 20° C. After 2.0 g of a 20% aqueous sulfuric acid solution and 5.0 g of toluene were added thereto, the mixture was stirred and then separated. The obtained organic layer was washed twice with 5.0 g of a 1% aqueous sodium hydroxide solution and once with 5.0 g of water, and concentrated under reduced pressure to give 1.1 g of 3-(2,6-dichloro-4-(3,3-dichloro-2-propenyloxy) phenoxy)-1-ethyl alcohol (purity: 95%, yield: 93%).

EXAMPLE 16

A mixture of 1.40 g of 3-bromopropanol, 10.0 g of toluene and 0.14 g of tetra-n-butylammonium bromide was heated to 60° C. Thereto was added dropwise a mixed solution of 2.0 g of 4-(3,3-dichloro-2-propenyloxy)phenol, 10.0 g of water and 1.49 g of a 27% aqueous sodium hydroxide solution with stirring over 6 hours. After completion of the addition, the mixture was further stirred for 11 hours at 60° C. In this period, 0.20 g of 3-bromopropanol and 0.20 g of a 27% aqueous sodium hydroxide solution were further added at the time point of 7 hours. Then, the reaction mixture was cooled to 20° C. After 4.0 g of a 20% aqueous sulfuric acid solution and 5.0 g of toluene were added thereto, the mixture was stirred and then separated. The obtained organic layer was washed once with 10.0 g of a 1% aqueous sodium hydroxide solution and once with 10.0 g of water, and concentrated under reduced pressure to give 2.5 g of 3-(4-(3,3-dichloro-2-propenyloxy)phenoxy)-1-propyl alcohol (purity: 93%, yield: 93%).

INDUSTRIAL APPLICABILITY

According to the process of the present invention, an alcohol compound useful as an intermediate for producing an active ingredient of insecticides can be produced efficiently with simple steps.

The invention claimed is:

1. A process for production of an alcohol compound represented by the formula (3):

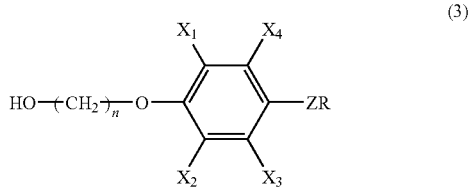

(3)

wherein $X_1$, $X_2$, $X_3$ and $X_4$ independently represent a hydrogen atom, a halogen atom or an alkyl group having 1 to 3 carbon atoms, Z represents an oxygen atom or a sulfur atom, R represents a halogen-substituted alkenyl group, and n represents an integer of 2 or 3; which comprises reacting a phenol represented by the formula (1):

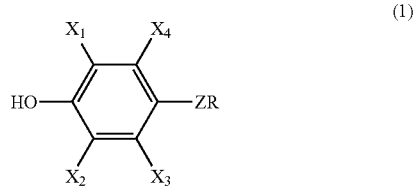

(1)

wherein $X_1$, $X_2$, $X_3$, $X_4$, Z and R are as defined above, with a haloalcohol represented by the formula (2):

(2)

wherein Y represents a chlorine atom or a bromine atom, and n is as defined above, in a biphase system composed of a water-immiscible organic solvent and an aqueous alkali metal hydroxide solution in the presence of a phase-transfer catalyst.

2. The process for production of an alcohol compound according to claim 1, wherein Z is an oxygen atom.

3. The process for production of an alcohol compound according to claim 1 or 2, wherein R is a 3,3-dihalo-2-propenyl group.

4. The process for production of an alcohol compound according to claim 1, wherein the water-immiscible organic solvent is a hydrocarbon compound or a chain ether compound.

5. The process for production of an alcohol compound according to claim 1, wherein the water-immiscible organic solvent is toluene.

6. The process for production of an alcohol compound according to claim 1, wherein a reaction temperature is 50° C. to 100° C.

7. The process for production of an alcohol compound according to claim 1, wherein the phase-transfer catalyst is a tetra-n-butylammonium salt.

8. The process for production of an alcohol compound according to claim 1, wherein the phenol represented by the formula (1) is 2,6-dichloro-4-(3,3-dichloro-2-propenyloxy)phenol.

9. The process for production of an alcohol compound according to claim 1, wherein n is 3.

10. The process for production of an alcohol compound according to claim 1, wherein the haloalcohol represented by the formula (2) is 3-bromo-1-propanol.

11. The process for production of an alcohol compound according to claim 2, wherein the water-immiscible organic solvent is a hydrocarbon compound or a chain ether compound.

12. The process for production of an alcohol compound according to claim 3, wherein the water-immiscible organic solvent is a hydrocarbon compound or a chain ether compound.

13. The process for production of an alcohol compound according to claim 2, wherein the water-immiscible organic solvent is toluene.

14. The process for production of an alcohol compound according to claim 2, wherein a reaction temperature is 50° C. to 100° C.

15. The process for production of an alcohol compound according to of claims 2, wherein the phase-transfer catalyst is a tetra-n-butylammonium salt.

16. The process for production of an alcohol compound according to claim 2, wherein the phenol represented by the formula (1) is 2,6-dichloro-4-(3,3-dichloro-2-propenyloxy)phenol.

17. The process for production of an alcohol compound according to claim 2, wherein n is 3.

18. The process for production of an alcohol compound according to claim 2, wherein the haloalcohol represented by the formula (2) is 3-bromo-1-propanol.

* * * * *